United States Patent
Asano et al.

(10) Patent No.: US 6,526,162 B2
(45) Date of Patent: *Feb. 25, 2003

(54) OPERATION ROUTE SEARCHING APPARATUS AND SEARCHING METHOD THEREOF

(75) Inventors: Takeo Asano, Kunitachi (JP); Akito Saito, Hino (JP); Takao Shibasaki, Tokyo (JP); Hiroshi Matsuzaki, Hachioji (JP)

(73) Assignee: Olympus Optical Co., Ltd., Tokyo (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/158,335

(22) Filed: Sep. 22, 1998

(65) Prior Publication Data

US 2001/0040991 A1 Nov. 15, 2001

(30) Foreign Application Priority Data

Sep. 26, 1997 (JP) .............................. 9-262138
Sep. 9, 1998 (JP) .......................... 10-254779

(51) Int. Cl.⁷ ................................................ G06K 9/00
(52) U.S. Cl. ...................................... 382/128; 600/300
(58) Field of Search ............................... 382/128, 129, 382/130, 131, 132, 288; 600/300

(56) References Cited

U.S. PATENT DOCUMENTS

| | | | |
|---|---|---|---|
| 4,630,203 A | * 12/1986 | Szirtes | 364/414 |
| 4,875,165 A | * 10/1989 | Fencil et al. | 364/413.22 |
| 4,984,159 A | * 1/1991 | Gullberg | 378/14 |
| 5,300,080 A | * 4/1994 | Calyman et al. | 600/130 |
| 5,551,434 A | * 9/1996 | Linuma | 128/661.09 |
| 5,638,819 A | 6/1997 | Manwaring et al. | |
| 5,855,553 A | * 1/1999 | Tajima et al. | 600/407 |
| 5,991,697 A | * 11/1999 | Nelson et al. | 702/49 |
| 6,047,080 A | * 4/2000 | Chen et al. | 382/128 |

FOREIGN PATENT DOCUMENTS

JP 3-162849 7/1991

* cited by examiner

Primary Examiner—Bhavesh Mehta
Assistant Examiner—Abolfazl Tabatabai
(74) Attorney, Agent, or Firm—Frishauf, Holtz, Goodman & Chick, P.C.

(57) ABSTRACT

The present invention writes the obtained two-dimensional image data of a body including a diseased portion in a computer or the like, and displays a three-dimensional image of the body including the diseased portion and the related data in the same monitor. The diseased portion data is then converted into a three-dimensional construction with use of a three-dimensional construction reconstructing section. The geometrical center of the three-dimensional constructed image is calculated by a geometrical center calculation section, and a plurality of linear lines or one linear line having the shortest distance directing from the geometrical center to the outside of the body is then calculated. The calculated line/lines is/are displayed to be overlapped on an image of the body including the diseased portion. In this manner, the present invention provides a stereotaxy operation route searching apparatus for showing a guideline of a low-invasive operation strategy to an operator, and the searching method.

36 Claims, 13 Drawing Sheets

OPERATION ROUTE SEARCHING APPARATUS AND SEARCHING METHOD THEREOF

BACKGROUND OF THE INVENTION

This invention relates to a system for constructing an image of a diseased portion of a patient as a three-dimensional image and determining an operation route on the basis of the three-dimensional image, in particular, an operation route searching apparatus for supporting the determination of an invasion route through which an instrument such as a puncturing needle is introduced into the body of the patient during an operation, and the searching method.

In general, it is very important problem for a surgical operation to specify a diseased portion of a patient, and to determine from what position outside the body and at what angle an instrument such as a puncturing needle is introduced into the body of the patient in order to approach the diseased portion.

For example, in the stereotaxy (the guided stereotaxy) which should be low-invasively performed, an operation instrument having a frame capable of precisely moving its own X, Y, and Z axes fixed to a head of the patient so as to surround the head. By adjusting scales on coordinates axes of a puncture guide instrument fixed to the frame of this operation instrument, the three-dimensional operation route in the three-dimensional space is determined, through which the instrument is introduced into the brain.

Prior to the introduction of the instrument into the brain of the patient, an operator specifies the position of the diseased portion in the brain on the basis of various data obtained in advance (with use of MRI, X-ray CT, and the like), and determines the most suitable introduction route (i.e., an operation route) through which an instrument such as a puncturing needle is introduced into the skull and guided to the diseased portion, and then performs the operation.

Most of examination data used as criteria of the determination of the route are, however, obtained from two-dimensional tomography films. The operator must grasp an outline of the diseased portion of the patient three-dimensionally and spatially from these numerous tomography films, imagine the three-dimensional image of the diseased portion, and determine an operation route and the actual operation plan from his/her own experience.

The determination of the operation route is not such a simple process as the mere determining of a linear invasion route. The operator must determine in the process whether or not there exists in the operation route any brain functional region, which administrates the functions of supporting the life, motions, or functions of the body, or any physiologically important region. The determination process is thus a very complicated work requiring a long period of time and so-experienced skill.

In order to support the operation route determination, a system for inputting the image data into a computer during the examination, thereby constructing the image data as a two-dimensional or three-dimensional computer graphics image has been proposed.

For example, the Published KOKAI Patent Application No. 3-162849 proposes a system for supporting the operation route determination. According to this system, a plurality of two-dimensional images obtained by a CT scanner are stacked to obtain a perspective image. Then, a diseased portion and an intended invasion position on the surface of a head, from which an instrument is introduced into the skull, are specified in the display of a monitor. Subsequently, the positional information of the operation route is input in the system. On the basis of the positional information, the operator calculates the puncturing needle invasion route spatially and displays it, thereby can determine whether or not the invasion route is the most suitable one.

According to this system, however, when any brain functional region or physiologically important region exists in the operation route calculated from the specified invasion position, the above-mentioned process must be repeated: specifying of the diseased portion and the intended invasion position; and calculating of the invasion route. The specifying process must be repeated till the specified operation route is found not to include any brain functional region or physiologically important region, and thus a very long period of time is required for the specifying process.

Further, in some actual operation, the operation route must inevitably pass through some of the brain functional regions or physiologically important regions depending on the position of the diseased portion in the head, wherever on the head surface the operation instrument invades from. The operator must thus determine which operation route attains the minimum invasion in every determination process of the operation route. The determination process therefore takes a very long period of time.

BRIEF SUMMARY OF THE INVENTION

The object of the present invention is to provide an operation route searching apparatus for searching an operation route by obtaining under various conditions a plurality of candidates of an invasion route through which an instrument such as a puncturing needle is introduced from the outside of the body to the diseased portion so as to three-dimensionally avoid regions the invasion into which may affect the body function of a patient and physiologically important regions of a patient, in order to show an operator a guideline for a strategy of a low-invasive and the most suitable operation, and a searching method thereof.

In order to attain the above-mentioned object, the present invention provides an operation route searching apparatus comprising: an input section for inputting a plurality of images obtained by tomography of a body including a diseased portion; a specifying section for allowing an operator to specify the diseased portion included in the images; a conversion section for converting the specified diseased portion into a three-dimensional structure; a geometrical center calculation section for calculating a geometrical center point of the three-dimensional structure as a center of the diseased portion; and a linear line calculation section for calculating a linear line as an operation route directed to the geometrical center point from outside of the body.

The present invention further provides an operation route searching method comprising: inputting a plurality of images obtained by tomography of a body including a diseased portion; enabling an operator to specify the diseased portion included in t he images; converting the specified diseased portion for each image into a three-dimensional structure; calculating a geometrical center point of the three-dimensional structure as a center of said diseased portion; and calculating a linear line as an operation route directed to the geometrical center point from outside of the body.

According to the operation route searching apparatus having the above-mentioned constitution and the searching method, a plurality of obtained two-dimensional image data are input into a computer or the like to be hierarchically displayed on a display. Among them, the diseased portion data is converted into a three-dimensionally constructed image and displayed. The geometrical center of the three-dimensionally constructed image is obtained by a calculation to obtain a plurality of linear lines directing from the geometrical center of the three-dimensional construction to the outside of the body or the shortest one of the linear lines. The lines or the shortest line is then displayed to be overlapped on the three-dimensional construction in order to provide an operator with a guideline for a low-invasive operation strategy.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

The embodiments of the present invention will be described in detail with reference to the drawings.

Figure 1:
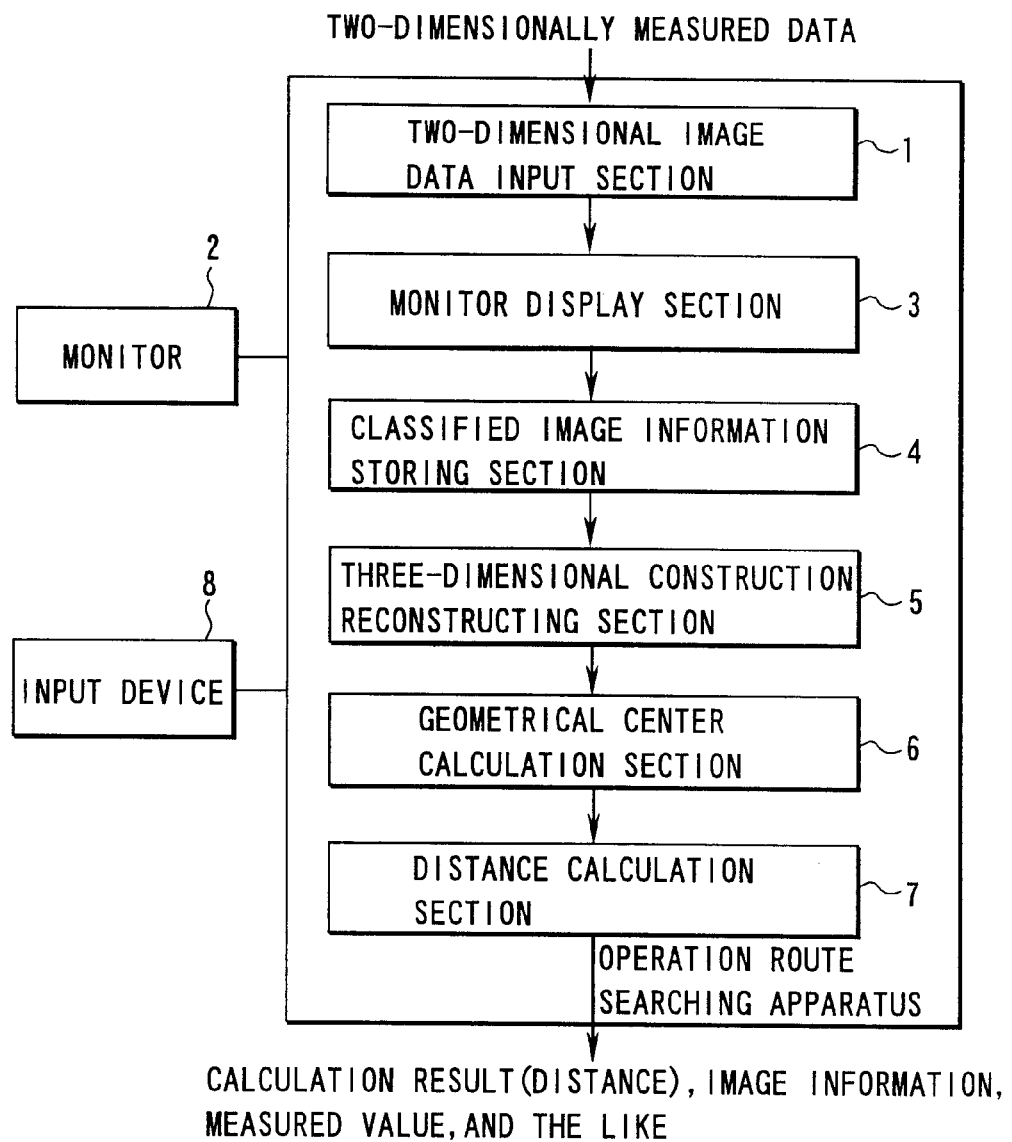
FIG. 1 shows a schematic structure of an operation route searching apparatus according to the first embodiment of the present invention.

FIG. 1 shows a schematic structure of an operation route searching apparatus according to the first embodiment of the present invention.

The operation route searching apparatus has a two-dimensional image data input section 1 for storing in a memory (not shown) of a computer various two-dimensionally examined data including the image of a diseased portion, which is obtained by an examination apparatus such as a MRI or an X-RAY CT. On the basis of the various data stored in the two-dimensional image data input section 1, the images of the diseased portion are simultaneously displayed by a monitor display section 3 of a monitor 2 to show hierarchically. The image data is added with information which is observed from the two-dimensional data and differs from tissue to tissue, and classified to be stored in a classified image information storing section 4. When an operator (surgeon or the like) of the apparatus specifies a data region (a diseased region) having a specific attribute by using the image information displayed in the monitor 2, the diseased region is reconstructed as a three-dimensional construction in a three-dimensional construction reconstructing section 5. The geometrical center of the reconstructed three-dimensional construction is calculated in a geometrical center calculation section 6 according to a calculation described later, and a distance from the geometrical center of the three-dimensional construction to the outside of the body (a position on the skin of the body) is calculated by a distance calculation section 7.

The apparatus is further provided with an input device 8 constituted of a mouse, a key board, and the like, from which the operator inputs an instruction and the like in the system. The results of the calculations, the image information, the measured values, and the like obtained by the apparatus of the present embodiment can be arbitrarily displayed in the monitor 2.

The following is the description of an embodiment in which the operation route searching apparatus of the present invention is applied to a stereotaxy operation as a typical example.

With reference to FIGS. 2, 3A, 3B, 3C, and 3D, the functions of the operation route searching apparatus having the above-mentioned constitution, and the calculation of the geometrical center of the diseased portion will be described below.

Figure 2:
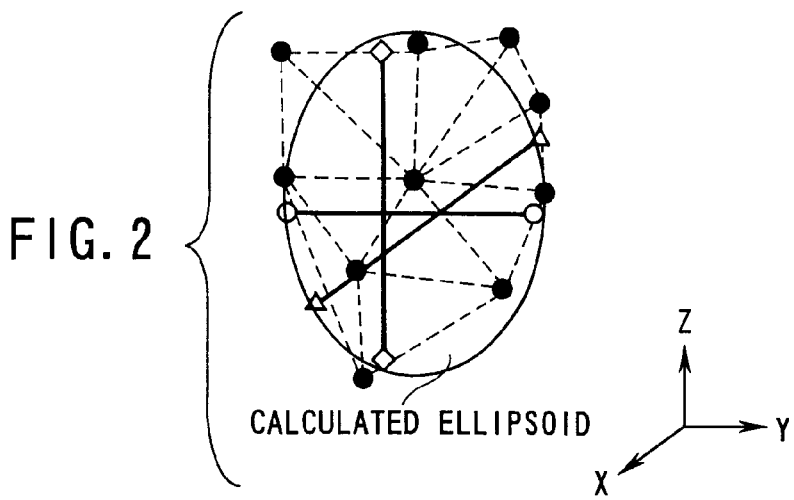
FIG. 2 is a schematic drawing for explaining a calculation method according to the first embodiment, of calculating a geometrical center of a diseased portion.

FIG. 2 shows the technical idea for explaining the calculation method of the geometrical center of the diseased portion according to the present embodiment, and FIGS. 3A–3D show an example of images displayed in the monitor 2 in the present embodiment.

Figure 3A:
FIGS. 3A, 3B, 3C, and 3D show an example of images displayed in a monitor according to the first embodiment.
Figure 3B:
Figure 3C:
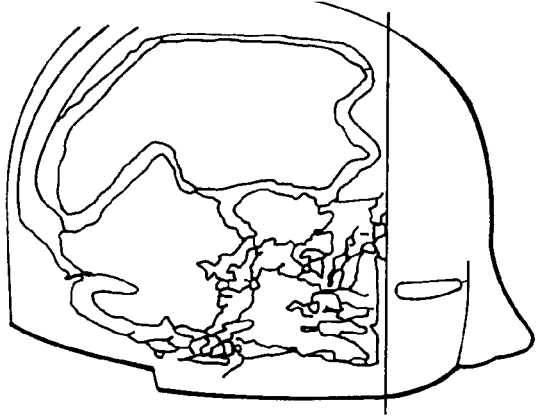
Figure 3D:
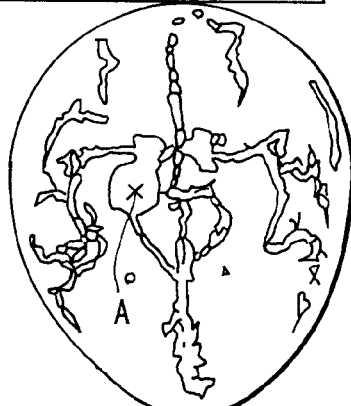

A point A indicated by a check mark × in FIG. 3D represents the geometrical center of the diseased portion, which is calculated by the calculation process described later, and values of X, Y, and Z, shown in a data region B of FIG. 3C represents a distance from the geometrical center to the surface of the head (a position on a skin of the body).

At first, the system operator (a surgeon) inputs the patient data obtained prior to the operation to the system of the present embodiment, and displays a two-dimensional image data in several stages at heights of the head (the body including the diseased portion) in a display (the same display) in the monitor 2 to construct a three-dimensional and thick head image (the image of the body including the diseased portion). The displays of the monitor 2 as shown in the drawings can be obtained by writing a program with use of a generally used programming language.

Each region of the image data is classified by tissue with use of attribute data (brightness and the like) shown in the head image. The brightness corresponds to the attribute of the tissue, and thus the classification of the tissues is performed in accordance with the brightness. The surgeon specifies the region of the diseased portion observed in the head image. By specifying the region of the diseased portion, the diseased portion can be displayed in the image to be more clearly or displayed in such a special shape that the position of the diseased portion can be easily specified, or in such a color that the portion can be easily discriminated from the other regions. Otherwise, only the specified diseased portion can be displayed as a three-dimensionally constructed image.

An example of the calculation method employed by the present embodiment, by which the geometrical center of the diseased portion is calculated, will be described below.

The image of the diseased portion specified by the operator of the system is prepared by the computer graphics. The geometrical shape thereof is a three-dimensional construction (an ellipsoid) as shown in FIGS. 3A–3D, the outermost of which is formed by connecting all control points which have the same data attribute.

At first of the calculation, all the coordinates data of the control points at the outermost forming the diseased portion region are searched. Among the control points, two control points the most spatially distant from of the x, y, and z axes as a standard in the system are selected for each of the axes and calculated. The distances between the two control points are set as variables of the three axes of the ellipsoid, and used to calculate the ellipsoid. In this manner, the diseased portion is approximated as an ellipsoid.

In this case, the three linear lines connecting the two control points in each axis extend in directions perpendicular to each other. Actually, the lines do not cross each other in most cases, but area of the diseased portion can be covered with the ellipsoid. The area of the diseased portion region can be thus calculated by a simple calculation. The present invention is therefore advantageous in this point. The center of the calculated ellipsoid is set as the geometrical center of the diseased portion and output to the distance calculation section 7.

The calculation method of calculating the distance from the center (the geometrical center) of the diseased portion to the head surface by the distance calculation section 7 will be described next.

The coordinates value of the calculated diseased portion center is already known. The operator roughly indicates a point on the head surface in the displayed image with use of a pointer of the mouse or cursor keys on the key board.

The linear line connecting the indicated point and the diseased portion center is calculated, and the point at which the linear line crosses the head surface is then calculated to calculate the distance between this crossing point and the diseased portion center. The calculated crossing point at the head surface is a point from which the instrument is introduced into the skull in the operation.

Figure 4:
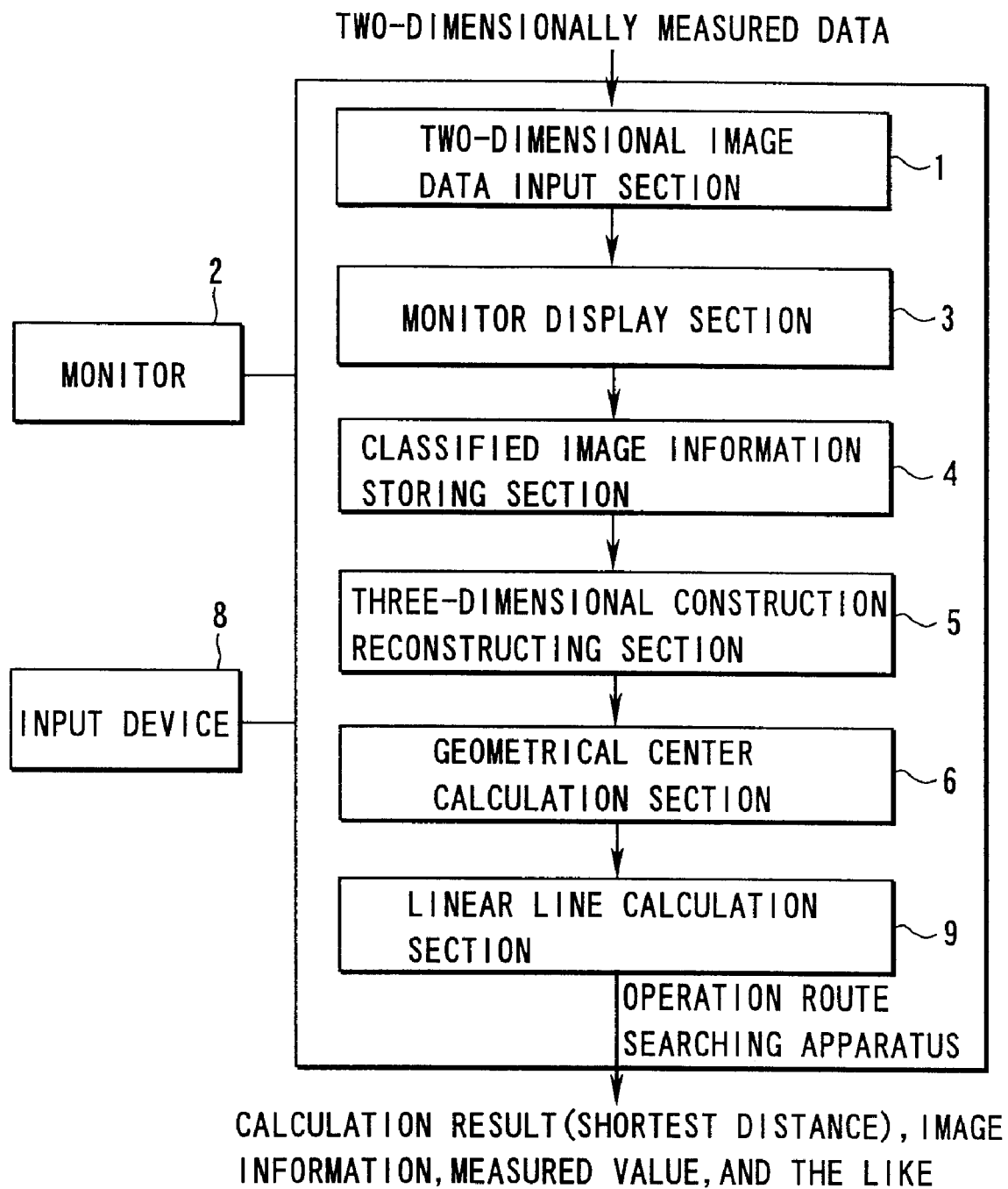
FIG. 4 shows a schematic structure of an operation route searching apparatus according to the second embodiment of the present invention.
Figures 5A, 5B:
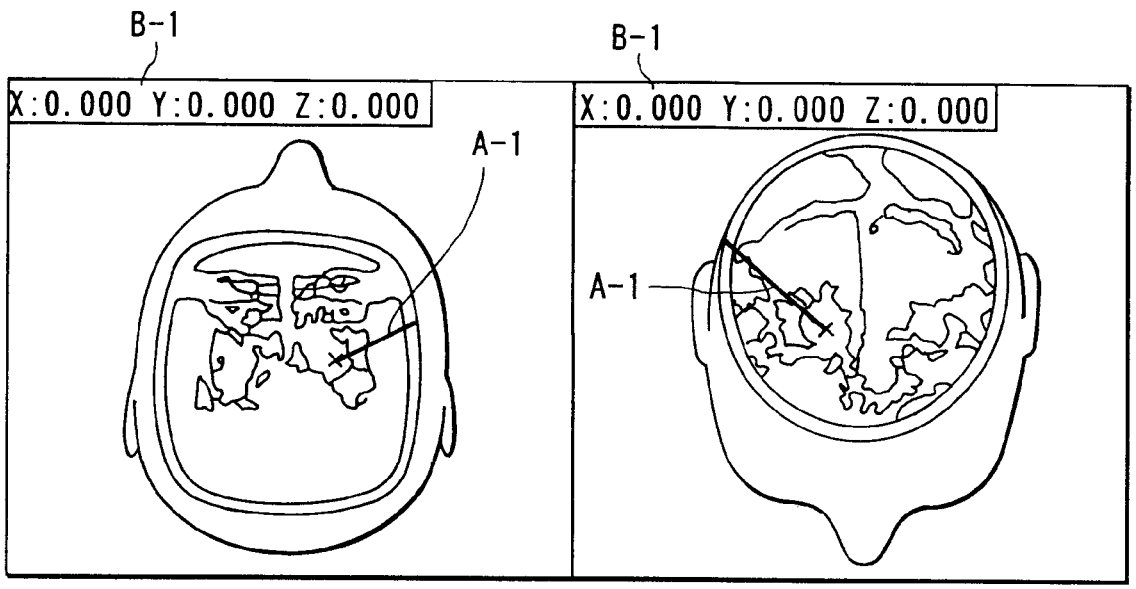
FIGS. 5A, 5B, 5C, and 5D show an example of images displayed in a monitor, in each of which the shortest linear operation route calculated in the second embodiment is shown to be overlapped on a three-dimensionally reconstructed image.
Figures 5C, 5D:
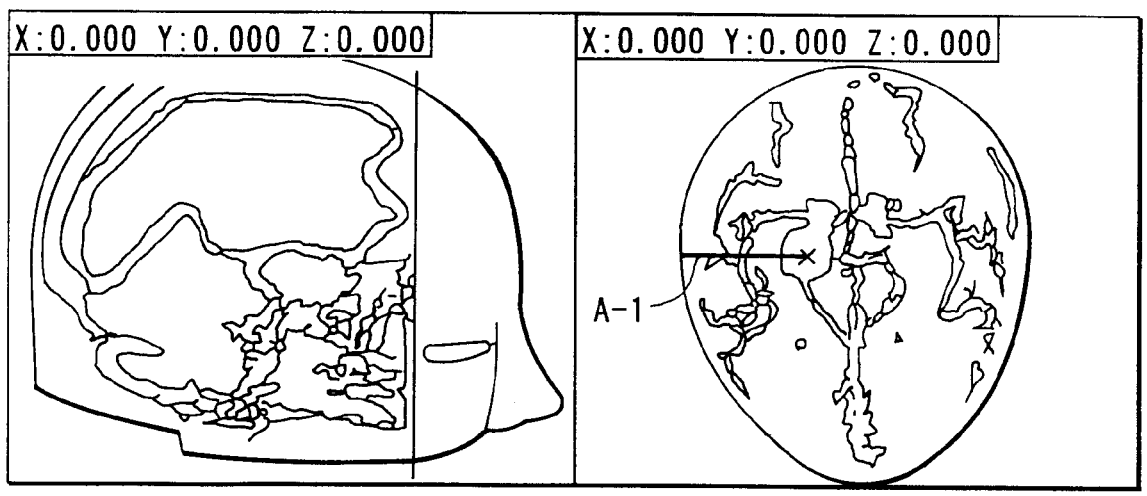

FIG. 4 shows the constitution of the operation route searching apparatus according to the second embodiment. The reference numerals used in the first embodiment are used to designate the same portions in this embodiment for simplicity of illustration, and the description thereof will be omitted.

The apparatus of the present embodiment has the same constitution as that of the first embodiment from the two-dimensional image data input section 1 to the geometrical center calculation section 6 in the first embodiment. In addition thereto, the apparatus is provided with a linear line calculation section 9.

In the present embodiment, obtained two-dimensional data input into the two-dimensional image data storing section 1 is subjected to various processings as performed in the first embodiment, and the diseased portion geometrical center calculation section 6 calculates the geometrical center of the diseased portion. The linear line calculation section 9 then calculates the shortest one of the linear lines connecting the calculated geometrical center and the head surface to display the shortest line in the monitor 2. FIGS. 5A–5D show one example of the images displayed in the monitor 2 of the present embodiment.

In the first embodiment, the distance from the diseased portion to a point specified by the surgeon at the head surface, is calculated. In the present embodiment, a linear route having a possibly shorter distance as one of the parameters specifying the operation route is selected as the linear operation route in order to attain the minimum invasion.

The present embodiment is intended to search the operation route having the shortest distance. According to the present embodiment, an operation route having the shortest distance among a plurality of operation routes connecting the diseased portion center and the head surface (i.e., the shortest one of the routes) can be calculated by the linear line calculation section 9, and displayed in the monitor as indicated as A-1 in FIGS. 5A, 5B, and 5D.

In short, according to the present embodiment, low-invasive and suitable operation route having the shortest distance can be searched.

Figure 6:
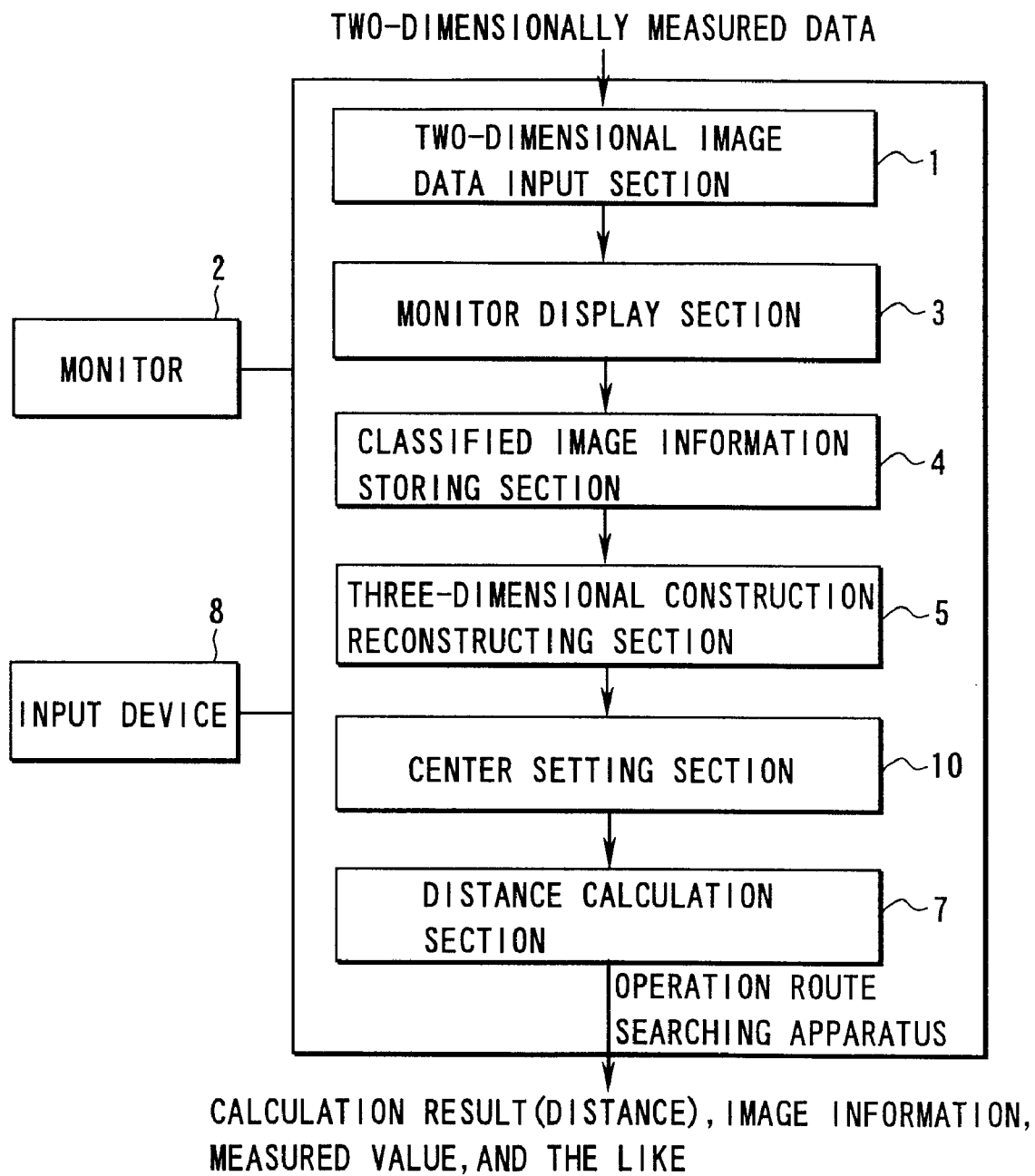
FIG. 6 shows a schematic structure of an operation route searching apparatus according to the third embodiment of the present invention.

FIG. 6 shows an example of the constitution of an operation route searching apparatus according to the third embodiment, which will be described below. In the apparatus of the present embodiment, the reference numerals used in the first embodiment are used to designate the same portions in this embodiment for simplicity of illustration, and the description thereof will be omitted.

The apparatus of the present embodiment has a constitution including the same element corresponding to those of the first embodiment from the two-dimensional image data input section 1 to the three-dimensional construction reconstructing section 5. In addition thereto, the center setting section 10 is newly provided to he apparatus.

According to the present embodiment, the center of the three-dimensionally reconstructed diseased portion is determined at the discretion of the operator (surgeon) of the system with use of the center setting section 10 during processing by the two-dimensional image data input section 1 to the three-dimensional construction reconstructing section 5, and the center of the three-dimensionally reconstructed diseased portion and the linear distance from the center of the diseased portion to an arbitrarily specified head surface point is calculated and output.

At first, the operator (surgeon) displays in the same display in the monitor 2 the two-dimensional image data based on the patient data obtained in advance, to show hierarchically with use of the apparatus of the present embodiment in order to construct a three-dimensional, thick, and perspective head image. Each region in the head image is classified by tissue in accordance with the brightness or the like shown in the image. The brightness data corresponds to each of the attributes of the tissues. The tissues thus can be classified according to the attributes on the basis of the brightness.

The surgeon specifies the diseased portion in the head image displayed in the monitor 2, and the center of the diseased portion (i.e., three-dimensional construction) at his/her own discretion. Unlike in the above-mentioned embodiments wherein the geometrical center is specified by the calculation, this method is advantageous in the case where it is preferable in consideration of the strategy of the operation that the surgeon arbitrarily sets the center of the diseased portion.

Next, the surgeon specifies a rough direction from the diseased portion center to the head surface, and the linear distance from the diseased portion to the head surface is calculated and displayed. The calculation result is displayed as shown in FIGS. 5A–5D.

Figure 7:
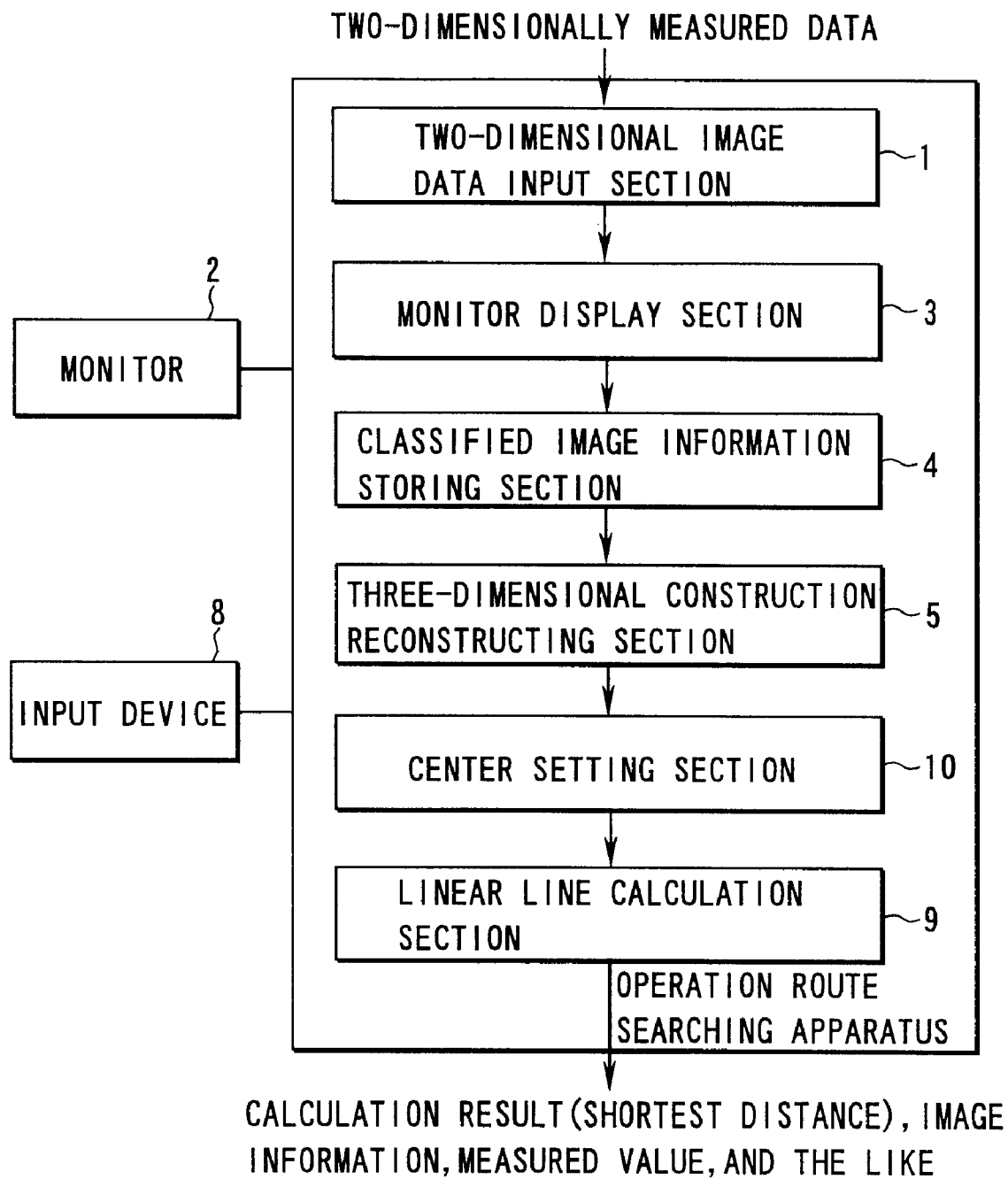
FIG. 7 shows a schematic structure of an operation route searching apparatus according to the fourth embodiment of the present invention.

FIG. 7 shows an example of the constitution of an operation route searching apparatus according to the fourth embodiment, which will be described below. The reference numerals used in the third embodiment are used to designate the same portions in this embodiment for simplicity of illustration, and, the description thereof will be omitted.

In the third embodiment, the operator (surgeon) specifies the center of the diseased portion and the direction of the direction of the head surface and calculates the linear distance therebetween. In the present embodiment, the shortest one of the routes from the center of the diseased portion to the head surface is specified by the operator (surgeon) to attain the minimum invasion.

Instead of the distance calculation section 7 shown in FIG. 6, the apparatus of the present embodiment is provided at the rear of the center setting section 10 with a linear line calculation section 9 for calculating the shortest one of the linear lines connecting the diseased portion center and the head surface.

The present embodiment is intended to search the shortest distance operation route from the arbitrarily set center of the diseased portion to the head surface. According to the present embodiment, the linear line calculation section 9 calculate a line having the shortest distance among a plurality of linear lines connecting the diseased portion and the head surface (i.e., the shortest operation route), and the shortest route is displayed in the monitor as shown in FIGS. 5A–5D.

As described above, according to the present embodiment, a low-invasive and suitable operation route having the shortest distance from the diseased portion center determined by the operator to the head surface can be searched.

Figure 8:
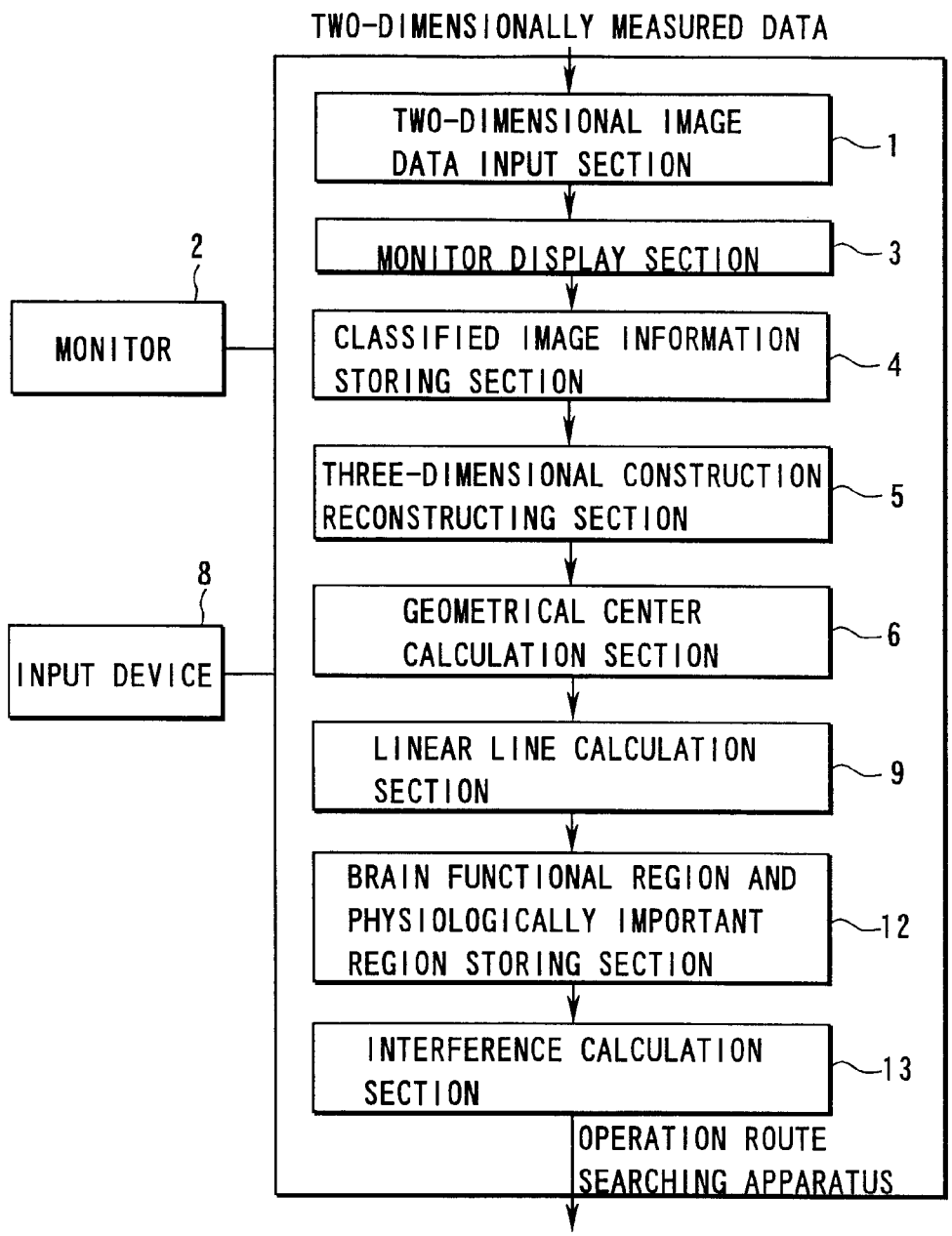
FIG. 8 shows a schematic structure of an operation route searching apparatus according to the fifth embodiment of the present invention.

FIG. 8 shows an example of the constitution of an operation route searching apparatus of the fifth embodiment. The reference numerals used in the fourth embodiment are used to designate the same portions in this embodiment for simplicity of illustration, and the description thereof will be omitted.

In addition to the constitution of the fourth embodiment, the apparatus of the present embodiment is provided with a brain functional region and physiologically important region storing section 12 for storing as data brain functional regions and physiologically important regions which support a life of the patient or the motions and the functions of the body; and an interference calculation section 13 for calculating the route not interfering the calculated shortest operation route.

The support by the apparatuses of the above-mentioned embodiments is to specify and determine the invasion route from the head surface to the diseased portion as a simple linear invasion route. In practical use, however, more complicated constraint conditions, for example, where the conservation of tissues and the invasion into the diseased portion need to be performed so as to possibly prevent the physiological functions of the patient from being damaged and to anatomically suppress the tissue damage at a minimum level.

One example of the interference calculation of the interference of the linear operation route in the brain functional regions and physiologically important regions in the present embodiment will be described below with reference to FIG. 9.

Figure 9:
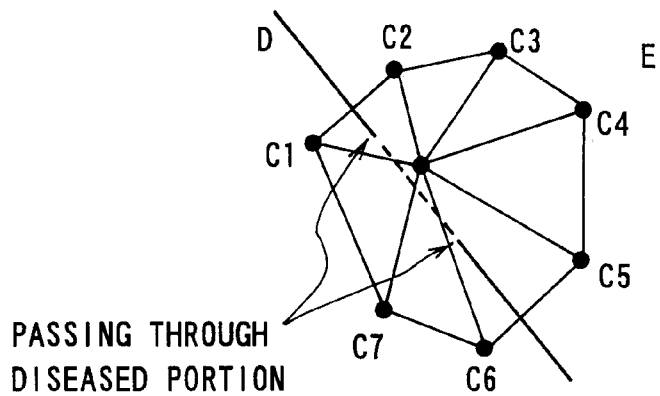
FIG. 9 is a schematic drawing for explaining an example of an interference calculation method according to the fifth embodiment, of calculating the interference of a linear operation route in brain functional regions and physiologically important regions.

As shown in FIG. 9, at the outermosts of the brain functional regions and physiologically important regions, which are set by the operator, control points C1–C8 contact to each other as at the outermost of the diseased portion. The region surrounded by the control points is divided into several minimum units each of which is formed by connecting at least three control points. The minimum units are each applied with a face. The region is thereby constituted three-dimensionally. The presence of the interface of a linear line D in the region can be clarified by calculating whether or not a linear line D passes through a face E formed by connecting the control points, in other words, whether or not a linear line is present in the face.

If the linear line D is present in the face, the linear line D is found to interfere in some brain functional regions or physiologically important regions. The apparatus then outputs another linear line not interfering in such a region.

More specifically, after executing similar processings to that in the above-mentioned embodiments, the brain functional regions and physiologically important regions (which are other than the diseased portion and not desirable to be invaded) are read from the brain functional region and physiologically important region storing section 12 for storing those regions as data, then overlapped on the three-dimensional construction image prepared as described above.

On the basis of the data read from the brain functional region and physiologically important region storing section 12, the interference calculation section 13 executes a calculation for determining whether or not linear lines proposed as the operation route interferes with the brain functional regions and the physiologically important regions in determining the operation route directed from the diseased portion center toward the head surface, and one of the linear lines which does not interfere in such a region is selected.

The selected linear line indicates the operation route. In this manner, the operator can obtain the optimum operation route.

As described above, the system of the present embodiment can search the operation route avoiding the brain functional regions and the physiologically important regions the damage of which may cause some anatomical problems, so as to maintain these regions with no damage.

Figure 10:
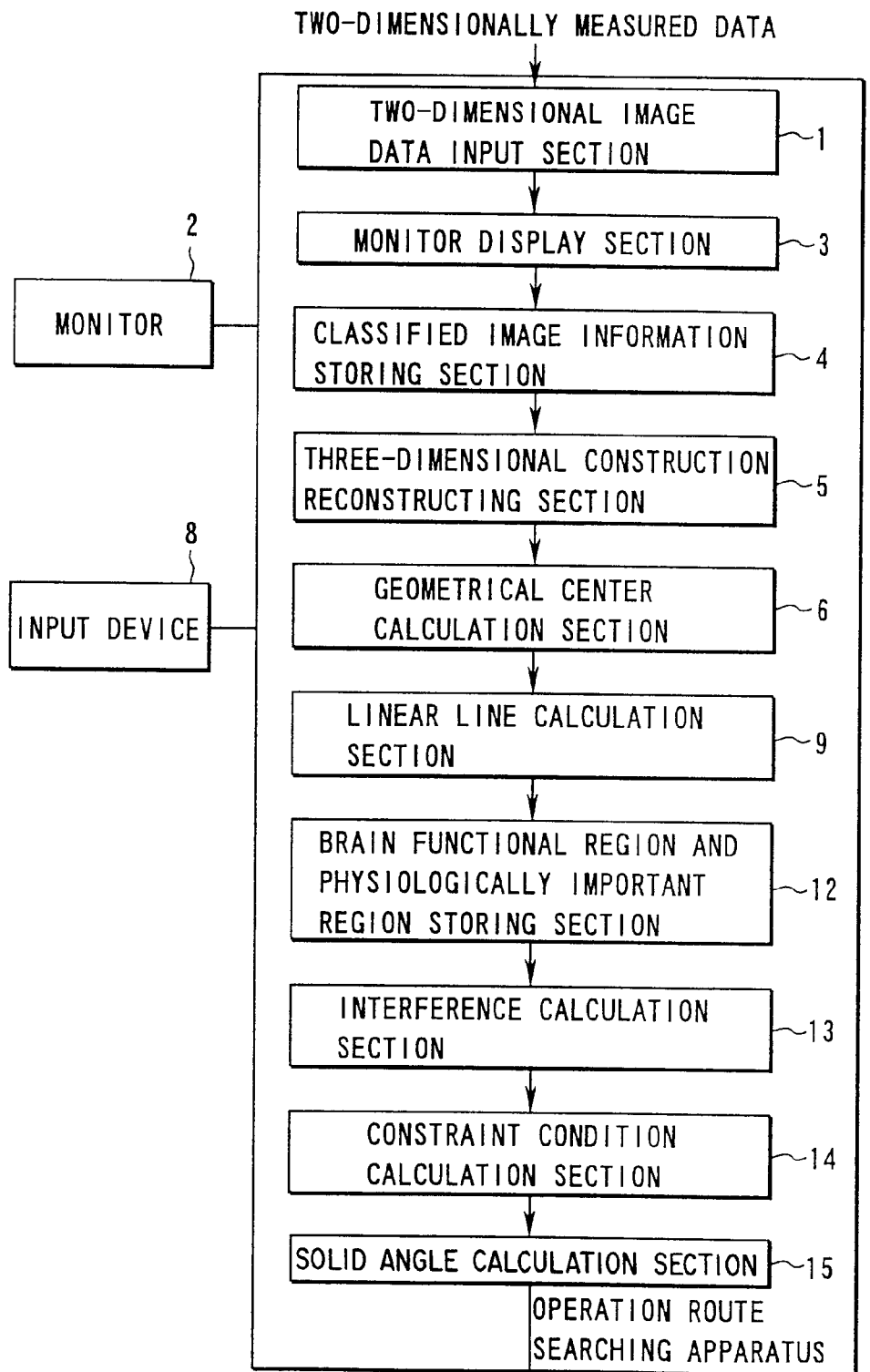
FIG. 10 shows a schematic structure of an operation route searching apparatus according to the sixth embodiment of the present invention.
Figures 11A, 11B:
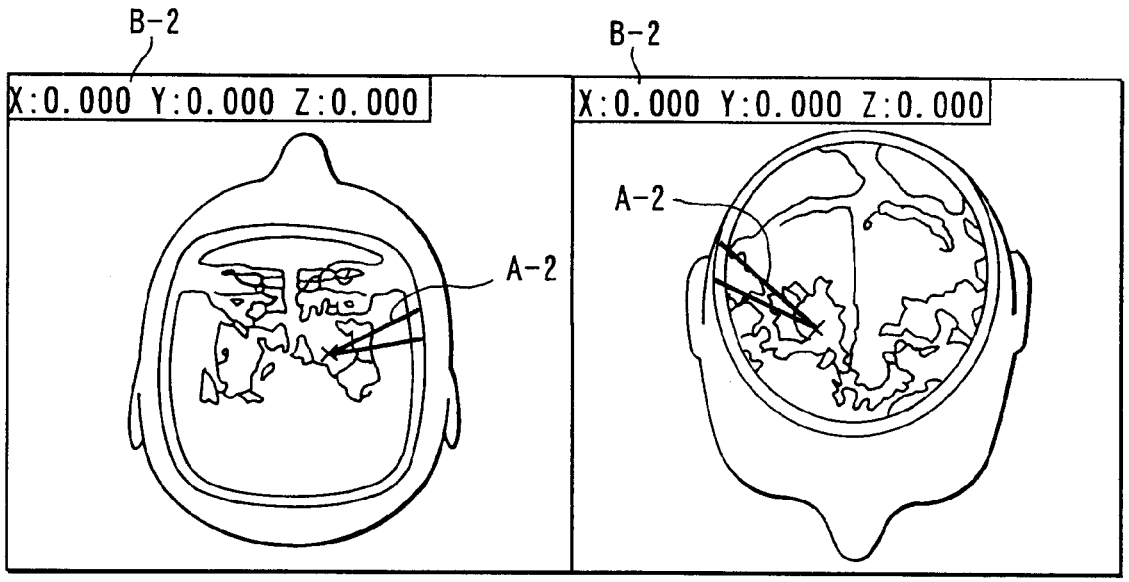
FIGS. 11A, 11B, 11C, and 11D show an example of images displayed in a monitor, each showing a region displayed in a cubic shape, which is calculated in the sixth embodiment is shown to be overlapped on a three-dimensionally reconstructed image.
Figures 11C, 11D:
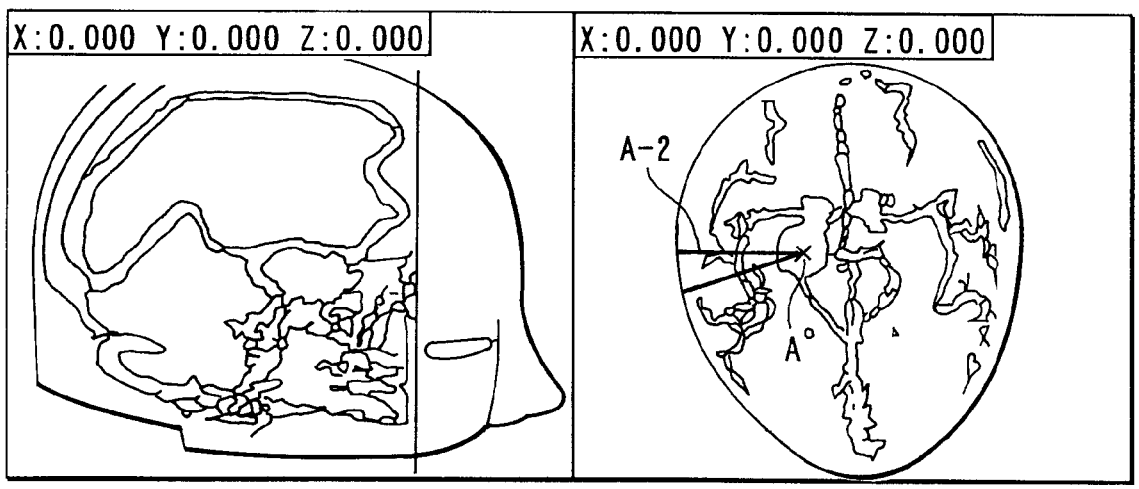

The following is the description of an example of the constitution of an operation route searching apparatus according to the sixth embodiment with reference to FIG. 10. The reference numerals used in the fifth embodiment are used to designate the same portions in this embodiment for simplicity of illustration, and the description thereof will be omitted.

The system of the present embodiment is provided at the rear of the interference calculation section 13 provided in the constitution of the fifth embodiment with a constraint condition calculation section 14 for adding a constraint condition to the calculation of determining whether or not linear lines as an operation route interfere in the brain functional regions and the physiologically important regions, and a solid angle calculation section 15 for calculating a solid angle formed of at least two of the linear lines calculated by the interference calculation section 13 and outputting it.

The constraint condition used in the present embodiment will be described below.

The determination of an invasion route (i.e., an operation route) is normally executed in consideration of the positional relationship between the diseased portion and the brain functional regions and the physiologically important regions. However, due to the position of the diseased portion in the brain, the route cannot help but inevitably being arranged very close to anatomically important regions in order to reach the diseased portion. In this case, if the operation route is determined so as not to interfere in the anatomically important regions, a sequela after the operation is not so critical in most cases though the length of the route is elongated in comparing with that of the routes not subjected to the interference calculation.

In order to search the better route in consideration of the above, the present invention inputs as a constraint condition a direction of a linear line for calculating the operation route or a region (i.e., a compensation value) which allows the minimum invasion, so as to use the direction or the compensation value in a re-calculation of the operation route.

FIGS. 11A–11D show an example of displays in each of which the region calculated by the present embodiment and represented in a solid angle is overlapped on the three-dimensionally reconstructed image by a three-dimensional construction reconstructing section 5.

In the drawings, a check mark A represents a geometrical center of the diseased portion, which is calculated by a processing, a linear line A-2 is a linear line output as a calculated operation route, and a data region B-2 represents data (distance, angle, and the like) of the calculated solid angle.

The present embodiment is intended to show the invasion route as a plane in order to recognize the invasion route attained by the fifth embodiment as a plane.

According to the present embodiment, an operator can select an invasion route having a higher free degree than that of the invasion route shown in a line.

Figure 12:
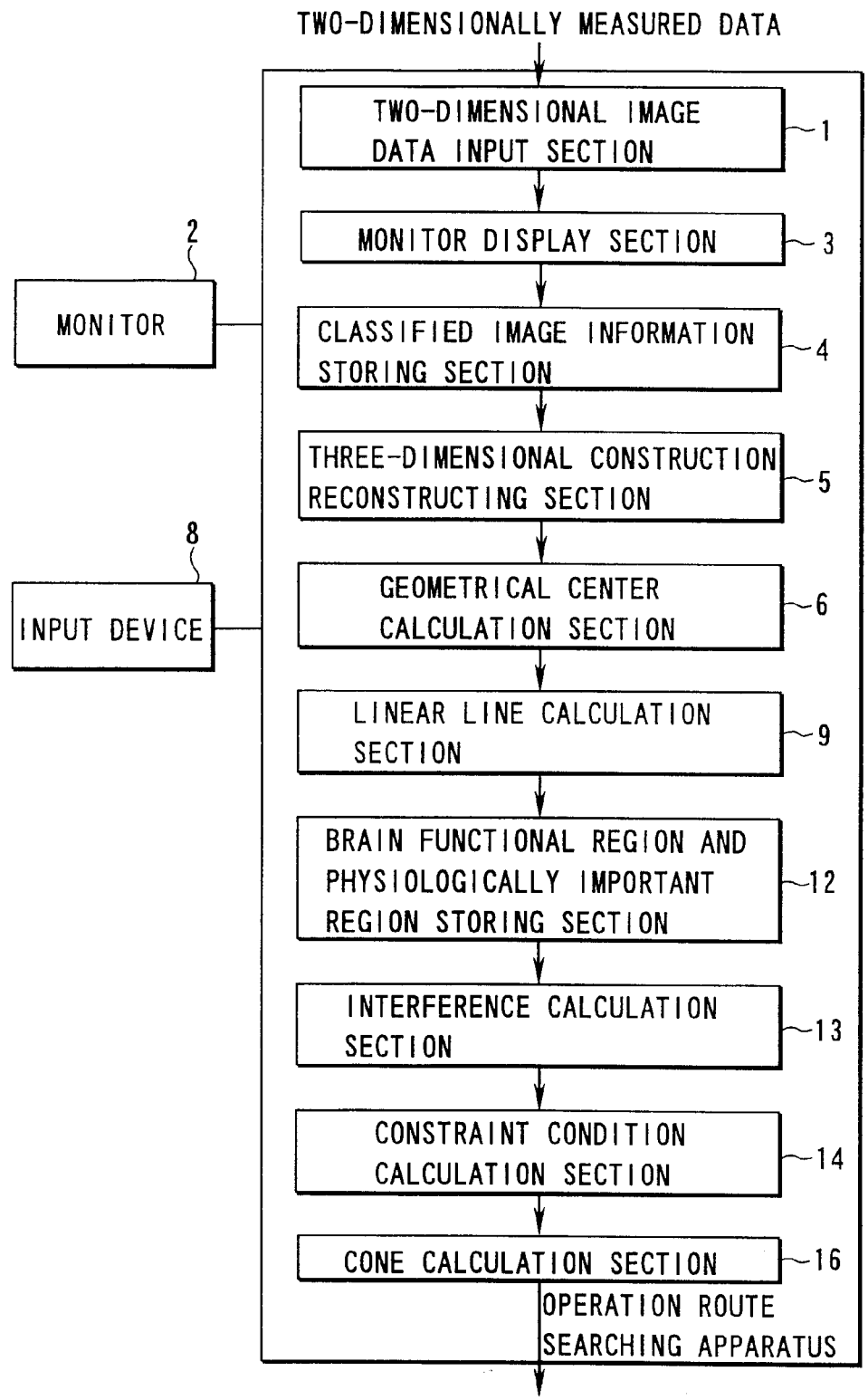
FIG. 12 shows a schematic structure of an operation route searching apparatus according to the seventh embodiment of the present invention.
Figures 13A, 13B:
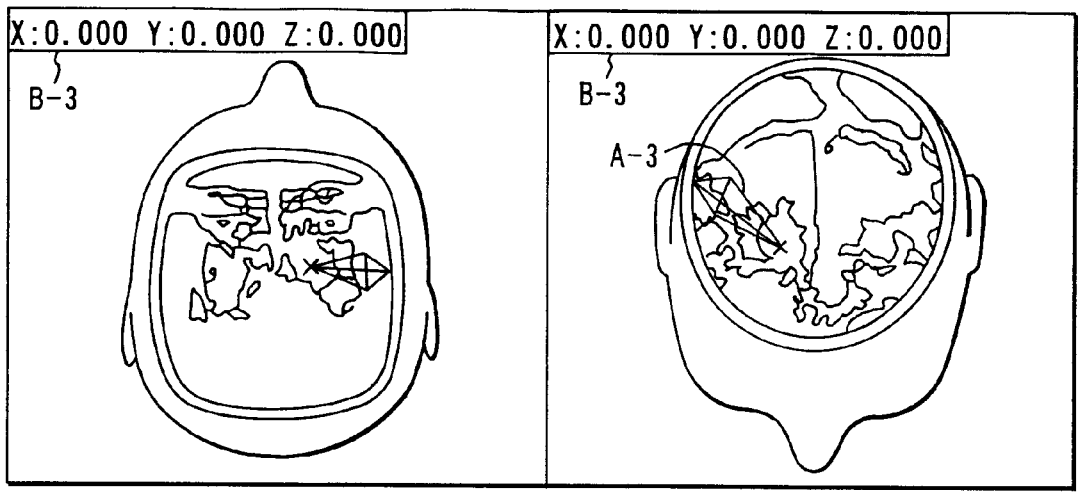
FIGS. 13A, 13B, 13C, and 13D show several examples of images displayed in a monitor, each showing a region displayed in a cone, which is calculated in the seventh embodiment is shown so as to be overlapped on a three-dimensionally reconstructed image.
Figures 13C, 13D:
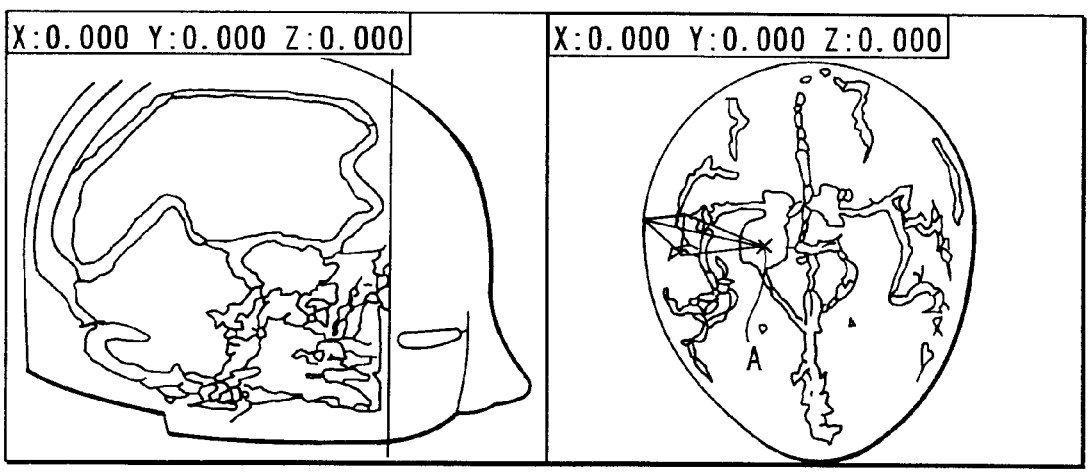

Next, a constitution of an operation route searching apparatus according to the seventh embodiment will be described with reference to FIG. 12. The reference numerals used in the sixth embodiment are used to designate the same portions in this embodiment for simplicity of illustration, and the description thereof will be omitted.

Instead of the solid angle calculation section 15 in the constitution of the sixth embodiment, for calculating the region of the operation route, the apparatus according to the present embodiment is provided with a cone calculation section 16 for calculating a cone region of an operation route, which is three-dimensionally formed by at least three linear lines.

The calculation of the operation route used in the present embodiment, by which the operation route is represented as a cone, will be described below.

Figure 14:
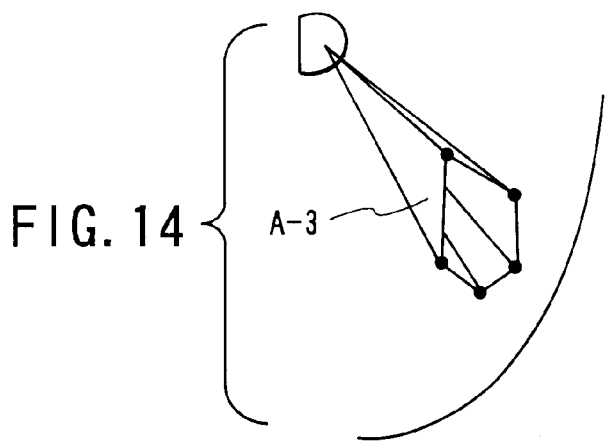
FIG. 14 is a schematic drawing for explaining an operation route according to the seventh embodiment, which is directed from a diseased portion center toward the surface of the head.

In the embodiments described above, the diseased portion center is specified, and a linear line connecting the diseased portion center and the head surface is determined as an operation route. The number of the linear lines directed from the diseased portion center to the head surface is, however, not limited to one as shown in FIG. 14, but several lines can be naturally obtained in the vicinity thereof if the constraint condition and the like are satisfied. The sectional view (i.e., a bottom face) of a bunch of the linear lines directed from the diseased portion center to the head surface is represented as a polygon on the head surface. The polygon is formed as a cone having a top at the diseased portion center, and a bottom on the head surface.

FIGS. 13A–13D show an example of displays for displaying the cone region calculated by the present embodiment so as to be overlapped on the image three-dimensionally reconstructed by the three-dimensional construction reconstructing section 5.

A check mark A indicated in the drawings represents the geometrical center of the diseased portion, which is calculated by a processing, a linear line A-3 is a linear line output as the calculated operation route, and a data region B-3 represents data (distance [the length of the side], angle, and the like) of the calculated cone.

According to the present embodiment, the region of the operation route is represented as a cone, thereby an invasion route can be three-dimensionally represented as a three-dimensional object formed of planes such that the invasion route obtained by the apparatus of the fifth embodiment can be recognized three-dimensionally. In this manner, an operator can select an invasion route having a higher free degree.

Figure 15:
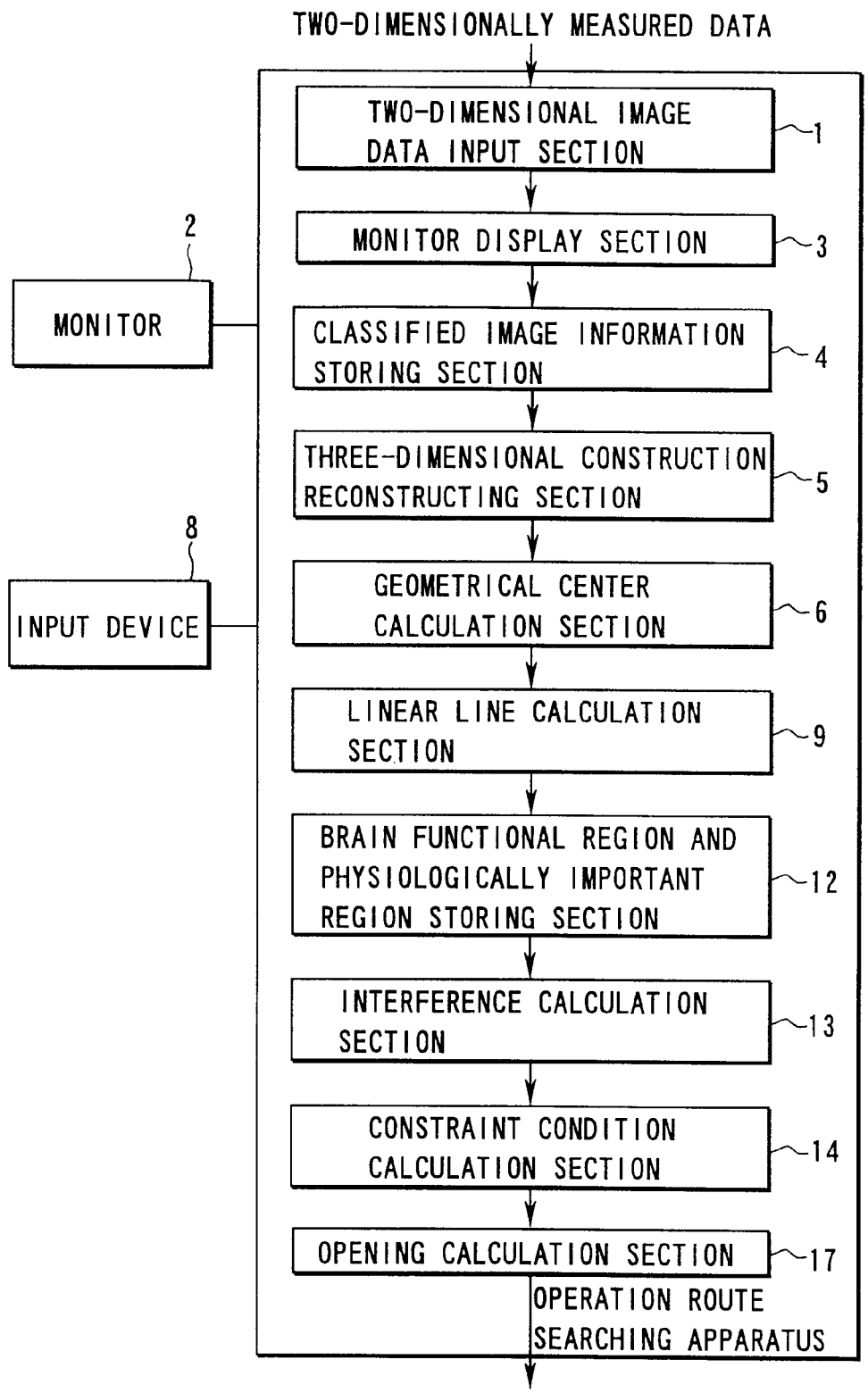
FIG. 15 shows a schematic structure of an operation route searching apparatus according to the eighth embodiment of the present invention.
Figures 16A, 16B:
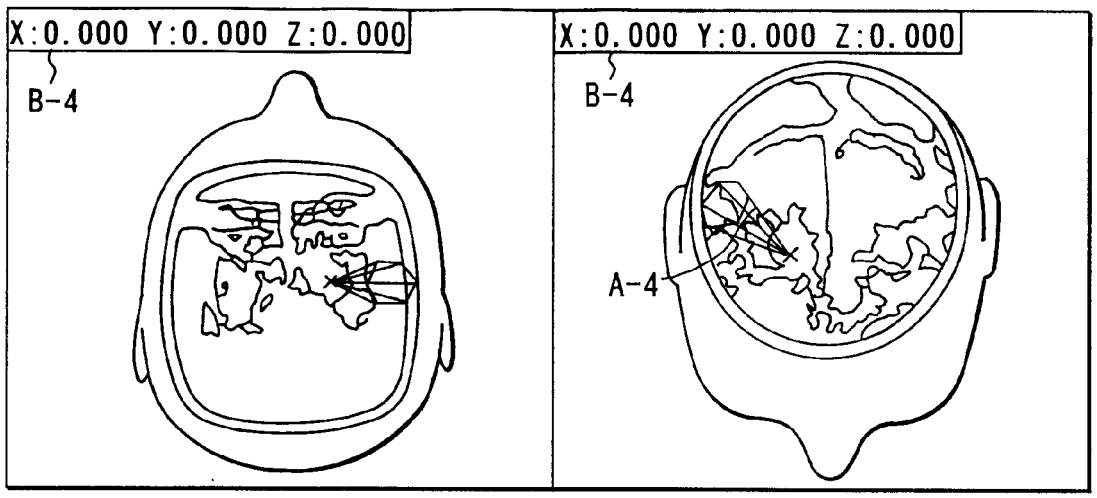
FIGS. 16A, 16B, 16C, and 16D show an example of images displayed in a monitor, each showing a region displayed in a polygon, which is calculated in the eighth embodiment is shown so as to be overlapped on a three-dimensionally reconstructed image.
Figures 16C, 16D:
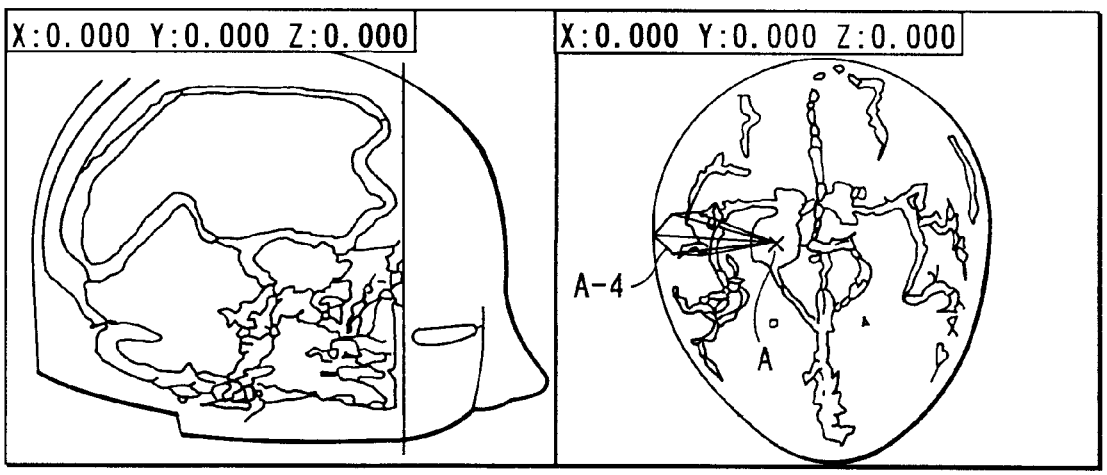

An example of a constitution of an operation route searching apparatus according to the eighth embodiment will be described next with reference to FIG. 15. The reference numerals used in the sixth embodiment are used to designate the same portions in this embodiment for simplicity of illustration, and the description thereof will be omitted.

Instead of the solid angle calculation section 15 for calculating the region of the three-dimensional operation route, which is provided to the constitution of the apparatus according to the sixth embodiment, the apparatus of the present embodiment is provided with an opening calculation section 17 for calculating a polygonal region of an operation route by calculating contact points of at least three linear lines and the head surface so as to show the region surrounded by the contact points as an opening of the head surface.

FIGS. 16A–16D show an example of displays in which a polygonal region calculated by the apparatus of the present embodiment is overlapped on the image three-dimensionally reconstructed by the three-dimensional construction reconstructing section 5.

In the drawings, a check mark A represents the geometrical center of the diseased portion, which is calculated by a processing, a linear line A-4 is a linear line output as a calculated operation route, and a data region B-4 represents data (distance [length of sides], angle, and the like) of the calculated cone.

With the elements as mentioned above, the apparatus of the present embodiment represents the operation route as a solid angle formed of planes such that the operation route constituted of several lines in the fifth embodiment can be recognized three-dimensionally, thereby can obtain the operation route having a higher free degree.

Next, the operation route searching apparatus of the ninth embodiment will be described with reference to FIG. 17.

In the seventh and the eighth embodiments, the processing is executed such that the bottom portion of the figure is arranged on the side of the head surface. Contrarily, a cone formed in the present embodiment has a top arranged on the side of the head surface, and a bottom portion arranged on the side of the diseased portion.

The cone in this embodiment represents a free operation area in the brain in which some degrees of the shaking of the distal end portion of at the operation instrument is allowed.

Figure 17:
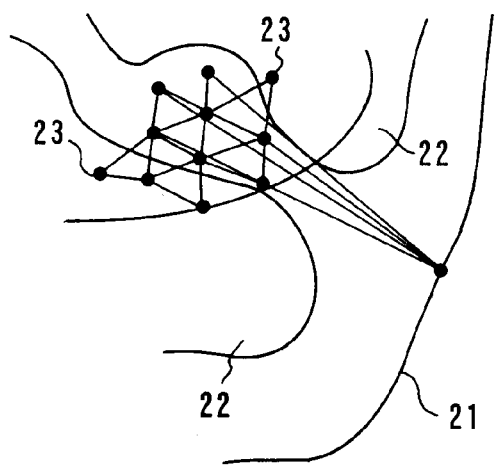
FIG. 17 shows a schematic drawing for explaining an operation route obtained by an operation route searching apparatus according to the ninth embodiment of the present invention.

In the present embodiment, the operation route is determined not by using the diseased portion center as used in the above-described embodiments, but by using linear lines connecting control points forming a surface of the diseased portion with the head surface, as shown in FIG. 17.

In this embodiment, there are a plurality of control points 23 forming the surface of the diseased portion. Among linear lines connecting the control points 23 with a point 21 which is roughly indicated on the head surface by the operator (surgeon), linear lines not interfering in the brain functional regions and the physiologically important regions 22 are selected. By using the non-interfering linear lines as ridge lines, the cone having the top arranged on the side of the head surface, and the bottom portion arranged on the side of the diseased portion can be attained.

The first to the ninth embodiments described above can be realized by a program prepared by using a programming language generally used in a processing unit such as a computer. The present invention can be realized not only by a computer used for a specific object but by a general-purpose computer by using the program stored in a portable recording medium such as an optomagnetic disk or a compact disk (CD-ROM).

As described above in detail, the present embodiment can provide a stereotaxy operation route searching apparatus for obtaining under various conditions a plurality of candidates of an invasion route through which an instrument such as a puncturing needle passes from the head surface to the diseased portion, so as to spatially avoid the brain functional regions and the physiologically important regions of a patient, and showing to an operator a guideline of a low-invasive and the optimum stereotaxy operation strategy, and the searching method.

In the above-mentioned embodiment, a stereotaxy operation route searching apparatus has been described to be specific. The operation route searching apparatus according to the present invention is, however, not limited to the applications to the bran operations as described above, but can be applied to a so-called endoscope which is an apparatus used for the operation of the body, and to an examination apparatus used for an examination requiring some introduction of an instrument into the body.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An operation route searching apparatus comprising:
    an input section for inputting a plurality of images obtained by tomography of a body including a diseased portion;
    a specifying section for allowing an operator to specify the diseased portion included in the images;
    a conversion section for converting the specified diseased portion into a three-dimensional structure;
    a geometrical center calculation section for calculating a geometrical center point of the three-dimensional structure as a center of the diseased portion; and
    a linear line calculation section for calculating a linear line as an operation route directed to the geometrical center point from outside of the body.

2. An operation route searching apparatus according to claim 1, wherein the linear line calculation section calculates a line having a shortest distance between the geometrical center point and a surface of the body from among other possible lines.

3. An operation route searching apparatus according to claim 1, wherein the specifying section allows the operator to specify the diseased portion in accordance with attributes of tissue regions.

4. An operation route searching apparatus according to claim 1, further comprising:
    a storing section for storing data indicating a predetermined tissue region; and
    an interference calculating section for calculating an interference between the linear line and the predetermined tissue region based on the data from the storing section.

5. An operation route searching apparatus according to claim 4, further comprising:
    a constraint condition adding section for defining a constraint condition used in the interference calculation.

6. An operation route searching apparatus according to claim 1, wherein the linear line calculation section calculates a plurality of linear lines.

7. A operation route searching apparatus according to claim 6, further comprising:
    a solid angle calculation section for calculating a solid angle formed by at least two of the linear lines.

8. An operation route searching apparatus according to claim 6, further comprising:
    a cone calculation section for calculating a cone formed by at least three of the linear lines.

9. An operation route searching apparatus according to claim 6, further comprising:

an area calculating section for calculating a size of a polygon formed by connecting crossing points of the linear lines and a surface of the body.

10. An operation route searching apparatus comprising:
an input section for inputting a plurality of images obtained by tomography of a body including a diseased portion;
a specifying section for allowing an operator to specify the diseased portion included in the images;
a conversion section for converting the specified diseased portion into a three-dimensional structure; and
a linear line calculation section for calculating a linear line as an operation route directed to a designated point within the three-dimensional structure from outside of the body.

11. An operation route searching apparatus according to claim 10, wherein the linear line calculation section calculates a line having a shortest distance between the designated point and a surface of the body from among other possible lines.

12. An operation route searching apparatus according to claim 10, wherein the specifying section allows the operator to specify the diseased portion in accordance with attributes of tissue regions.

13. An operation route searching apparatus according to claim 10, further comprising:
a storing section for storing data indicating a predetermined tissue region; and
an interference calculating section for calculating an interference between the linear line and the predetermined tissue region based on the data from the storing section.

14. An operation route searching method comprising:
inputting a plurality of images obtained by tomography of a body including a diseased portion;
enabling an operator to specify the diseased portion included in the images;
converting the specified diseased portion into a three-dimensional structure;
calculating a geometrical center point of the three-dimensional structure as a center of said diseased portion; and
calculating a linear line as an operation route directed to the geometrical center point from outside of the body.

15. An operation route searching method according to claim 14, wherein the calculated linear line is a line having a shortest distance between the geometrical center point and a surface of the body from among other possible lines.

16. An operation route searching method according to claim 14, wherein the operator is enabled to specify the diseased portion in accordance with attributes of tissue regions.

17. An operation route searching method according to claim 14, further comprising:
storing data indicating a predetermined tissue region; and
calculating an interference between the linear line and the predetermined tissue region based on the stored data.

18. An operation route searching method according to claim 17, further comprising:
defining a constraint condition used in the interference calculation.

19. An operation route searching method according to claim 14, wherein a plurality of linear lines are calculated as operation routes.

20. An operation route searching method according to claim 19, further comprising:
calculating a solid angle formed by at least two of the linear lines.

21. An operation route searching method according to claim 19, further comprising:
calculating a cone formed by at least three of the linear lines.

22. An operation route searching method according to claim 19, further comprising:
calculating a size of a polygon formed by connecting crossing points of the linear lines and a surface of the body.

23. An operation route searching method comprising:
inputting a plurality of images obtained by tomography of a body including a diseased portion;
enabling an operator to specify the diseased portion included in the images;
converting the specified diseased portion into a three-dimensional structure; and
calculating a linear line as an operation route directed to a designated point within the three-dimensional structure from outside of the body.

24. An operation route searching method according to claim 23, wherein the calculated linear line is a line having a shortest distance between the geometrical center point and a surface of the body from among other possible lines.

25. An operation route searching method according to claim 23, wherein the operator is enabled to detect the diseased portion in accordance with attributes of tissue regions.

26. An operation route searching method according to claim 23, further comprising:
storing data indicating a predetermined tissue region; and
calculating an interference between the linear line and the predetermined tissue region based on the stored data.

27. A recording medium having stored thereon a searching program for causing a computer to execute an operation route searching process comprising:
inputting into the computer a plurality of images obtained by tomography of a body including a diseased portion;
enabling an operator to specify the diseased portion included in the images;
converting the specified diseased portion into a three-dimensional structure;
calculating a geometrical center point of the three-dimensional structure as a center of said diseased portion; and
calculating a linear line as an operation route directed to the geometrical center point from outside of the body.

28. A recording medium according to claim 27, wherein the process further comprises:
storing data indicating a predetermined tissue region; and
calculating an interference between the linear line and the predetermined tissue region based on the stored data.

29. A recording medium according to claim 27, wherein a plurality of linear lines are calculated as operation routes.

30. A recording medium according to claim 29, wherein the process further comprises:
calculating a solid angle formed by at least two of the linear lines.

31. A recording medium according to claim 29, wherein the process further comprises:
calculating a cone formed by at least three of the linear lines.

32. A recording medium according to claim 29, wherein the process further comprises:

calculating a size of a polygon formed by connecting crossing points of the linear lines and a surface of the body.

33. A recording medium having stored thereon a searching program for causing a computer to execute an operation route searching process comprising:

inputting a plurality of images obtained by tomography of a body including a diseased portion;

enabling an operator to specify the diseased portion included in the images;

converting the specified diseased portion into a three-dimensional structure; and calculating a linear line directed as an operation route directed to a designated point within the three dimensional structure from outside of the body.

34. A recording medium according to claim 33, wherein the calculated linear line is a line having a shortest distance between the geometrical center point and a surface of the body from among other possible lines.

35. A recording medium according to claim 33, wherein the operator is enabled to specify the diseased portion in accordance with attributes of tissue regions.

36. A recording medium according to claim 33, wherein the process further comprises:

storing data indicating a predetermined tissue region; and calculating an interference between the linear line and the predetermined tissue region based on the stored data.

* * * * *